United States Patent

Fogarty et al.

Patent Number: 6,039,712
Date of Patent: *Mar. 21, 2000

[54] IMPLANTABLE INJECTION PORT

[75] Inventors: Terence M. Fogarty, 1830 River Ridge Rd., Hudson, Wis. 54016; Robert A. Arp, Eden Prairie, Minn.

[73] Assignee: Terence M. Fogarty, Hudson, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/964,473

[22] Filed: Nov. 4, 1997

[51] Int. Cl.⁷ .................................................. A61M 11/00
[52] U.S. Cl. .......................... 604/93; 604/175; 604/891.1
[58] Field of Search ........................... 604/93, 175, 891.1

[56] References Cited

U.S. PATENT DOCUMENTS

| | | | |
|---|---|---|---|
| 4,543,088 | 9/1985 | Bootman et al. | 604/93 |
| 4,569,675 | 2/1986 | Prosl et al. | 604/175 |
| 4,673,394 | 6/1987 | Fenton, Jr. et al. | 604/175 |
| 4,704,103 | 11/1987 | Stober et al. | 604/175 |
| 4,710,174 | 12/1987 | Moden et al. | 604/175 |
| 4,723,948 | 2/1988 | Clark et al. | 604/283 |
| 4,738,657 | 4/1988 | Hancock et al. | 604/93 |
| 4,762,517 | 8/1988 | McIntyre et al. | 604/175 |
| 4,767,410 | 8/1988 | Moden et al. | 604/175 |
| 4,772,270 | 9/1988 | Wiita et al. | 604/175 |
| 4,778,452 | 10/1988 | Moden et al. | 604/93 |
| 4,781,680 | 11/1988 | Redmond et al. | 604/93 |
| 4,781,695 | 11/1988 | Dalton | 604/175 |
| 4,798,584 | 1/1989 | Hancock et al. | 604/93 |
| 4,802,885 | 2/1989 | Weeks et al. | 604/93 |
| 4,834,720 | 5/1989 | Blinkhorn | 604/244 |
| 4,840,615 | 6/1989 | Hancock et al. | 604/93 |
| 4,861,341 | 8/1989 | Woodburn | 604/715 |
| 4,880,414 | 11/1989 | Whipple | 604/283 |
| 4,904,241 | 2/1990 | Bark | 604/93 |
| 4,929,236 | 5/1990 | Sampson | 604/175 |
| 4,969,873 | 11/1990 | Steinbach et al. | 604/93 |
| 5,013,298 | 5/1991 | Moden et al. | 604/93 |
| 5,026,344 | 6/1991 | Dijkstra et al. | 604/93 |
| 5,041,098 | 8/1991 | Loiterman et al. | 604/175 |
| 5,045,060 | 9/1991 | Malsky et al. | 604/93 |
| 5,053,013 | 10/1991 | Ensminger et al. | 604/167 |
| 5,090,954 | 2/1992 | Geary | 604/29 |
| 5,108,377 | 4/1992 | Cone et al. | 604/175 |
| 5,137,529 | 8/1992 | Watson et al. | 604/891.1 |
| 5,158,547 | 10/1992 | Doan et al. | 604/93 |
| 5,185,003 | 2/1993 | Brethauer | 604/93 |
| 5,207,644 | 5/1993 | Strecker | 604/93 |
| 5,213,574 | 5/1993 | Tucker | 604/93 |
| 5,263,930 | 11/1993 | Ensminger | 604/93 |
| 5,318,545 | 6/1994 | Tucket | 604/244 |
| 5,324,518 | 6/1994 | Orth et al. | 424/423 |
| 5,328,465 | 7/1994 | Kratoska et al. | 604/93 |
| 5,336,194 | 8/1994 | Polaschegg et al. | 604/175 |
| 5,360,407 | 11/1994 | Leonard | 604/175 |
| 5,387,192 | 2/1995 | Glantz et al. | 604/93 |
| 5,476,460 | 12/1995 | Montalvo | 604/891.1 |
| 5,562,618 | 10/1996 | Cai et al. | 604/93 |
| 5,613,945 | 3/1997 | Cai et al. | 604/93 |

*Primary Examiner*—Wynn Wood Coggins
*Assistant Examiner*—N. Kent Gring

[57] ABSTRACT

An implantable injection port consists of a very low profile housing with virtually no residual volume while maintaining a large target area for the needle.

18 Claims, 5 Drawing Sheets

IMPLANTABLE INJECTION PORT

BACKGROUND OF THE INVENTION

1. Field of the Invention

This invention relates to an implantable injector port and connector for use with an implantable catheter, for delivery of medications or nutrients to the vascular system or for blood sampling.

2. Description of the Related Art

Implantable injection ports are provided under the patient's skin and receive medication infused through a patient's skin via a hypodermic needle. The injection ports provide a resealable septum and a housing to temporarily hold the medication before it proceeds via a catheter to the selected site in the patient. Montaivo, U.S. Pat. No. 5,476,460 teaches an infusion port with a substantially reduced internal volume through the use of inert beads which substantially fill the housing chamber. Low profile injection ports are also described in Cone et al., U.S. Pat. No. 5,108,377.

None of the prior art injection ports provide a port that provides a low profile, a large septum that can withstand high operating pressures, a housing connector assembly without welding, soldering or bonding, light weight, very low residual volume and a connector flange that is collapsed, not press fit with galled surfaces.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides an implantable injection port with a residual volume that is minimized. This is accomplished by:

providing no reservoir chamber, providing a housing with a base that is not penetrable with a needle, providing a solid material next to the base that is needle penetrable, and has a thickness to accommodate the needle point cutting edge where the needle cannula is not substantially radially defined, providing a non-solid element that is needle penetrable, that is a fluid passage in communication with the housing connector aperture and the needle cannula, and is located at the elevation where the needle cannula is substantially defined radially and the housing connector aperture is located, (note: the connector flange is shorter than the corresponding depth of the housing connector aperture, so the elevation of the fluid passage at the connector is the same as the connector aperture in the housing), providing a septum assembly that seals the entrance to the housing, providing a filter or volume displacement element in connector filter chamber.

This invention may be utilized to provide implantable injection ports for the administration of medications or nutrients or blood sampling. Specifically it may be used for injection ports having the following features:

Low profile, for example overall heights of less than 1 cm.

Large septum (needle target), for example 2 cm diameter. High operating pressures in excess of 100 psi. Very low residual volumes, for example 0.20 ml with a 2 cm septum. Very light weight, for example an injection port having a 2 cm septum, with a titanium housing and connector weighs 11.5 grams, with a polysulfone housing and connector weighs 5.5 grams. Needle access to the septum can vary up to 60° from perpendicular. Requiring no welding, soldering or adhesive bonds. Provision for a filter while keeping a low residual volume.

BRIEF DESCRIPTION OF THE DRAWINGS

A detailed description of the invention is hereafter described with specific reference being made to the drawings in which.

DESCRIPTION OF THE PREFERRED EMBODIMENTS

Apparatus and Method

Figure 1:
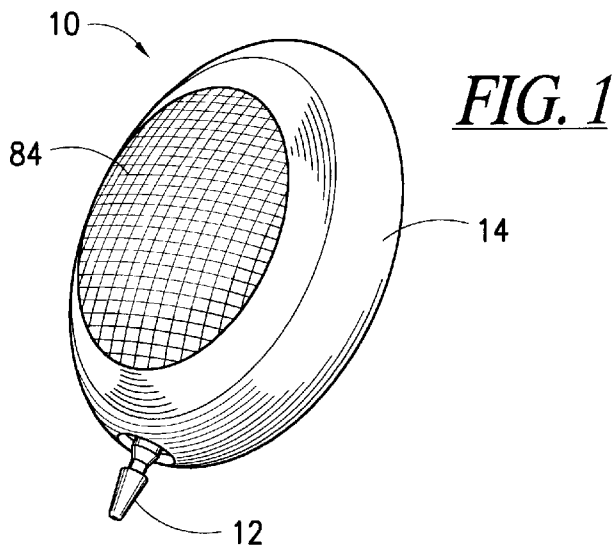
FIG. 1 is a perspective view of the injection port.
Figure 2:
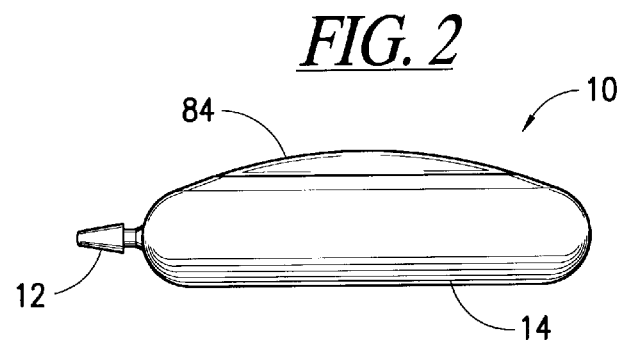
FIG. 2 is a side view of the injection port.
Figure 3:
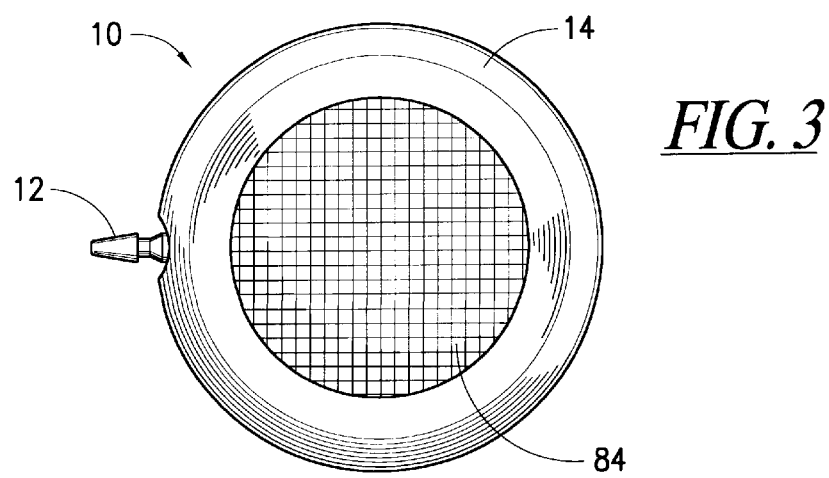
FIG. 3 is a top view of the injection port.

The inventive injection port 10 and connector 12 attachment are shown in FIGS. 1 to 10. FIGS. 1–3 show the general appearance of the injection port 10 and the small relative size of the connector 12. The injection port housing 14 and connector 12 may be fabricated in metal or plastic, and should be the same materials. The preferred metal is titanium and the preferred plastic is polysulfone. If the housing 14 and connector 12 are metal, and if a metal filter is used, it should also be a material of the same nobility as the housing 14 and connector 12 to prevent corrosion.

The dimensions of the interference fit of the connector 12 and housing 14 for this application is 0.0015 to 0.0030 inch, preferably 0.0015–0.0025 inch. The connector flange 18 major diameter is 0.0015 to 0.0030 inch larger that the corresponding minor diameter of the housing aperture 16.

Figure 9:
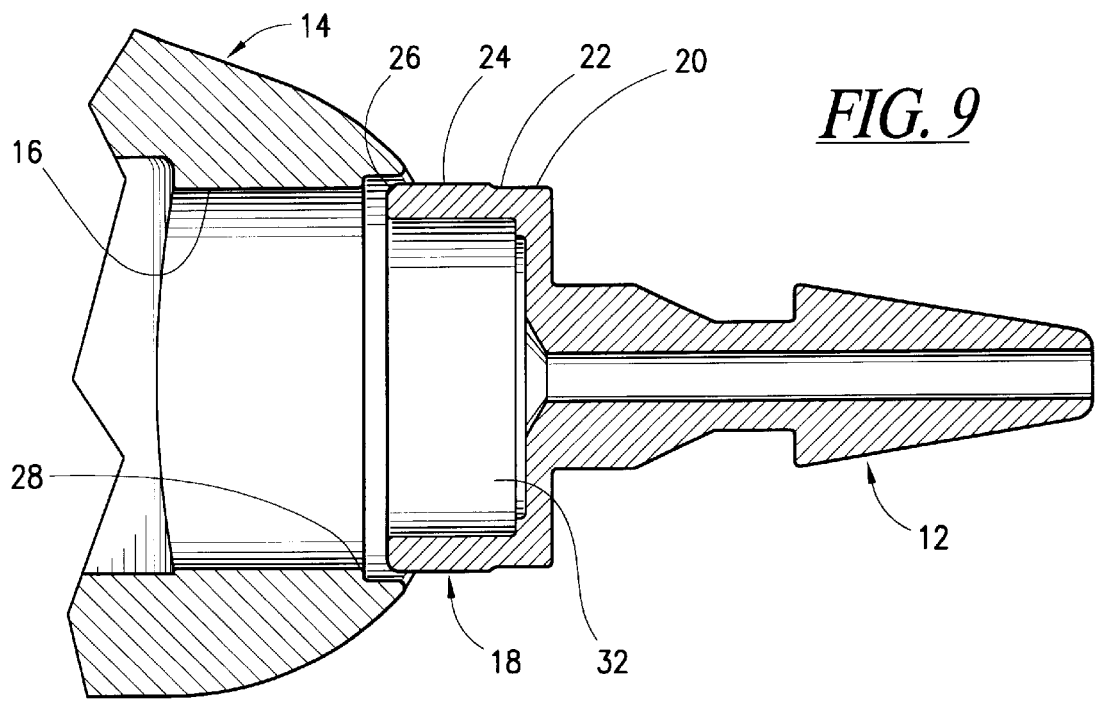
FIG. 9 is a cross-sectional, enlarged view of the housing and connector during assembly.
Figure 10:
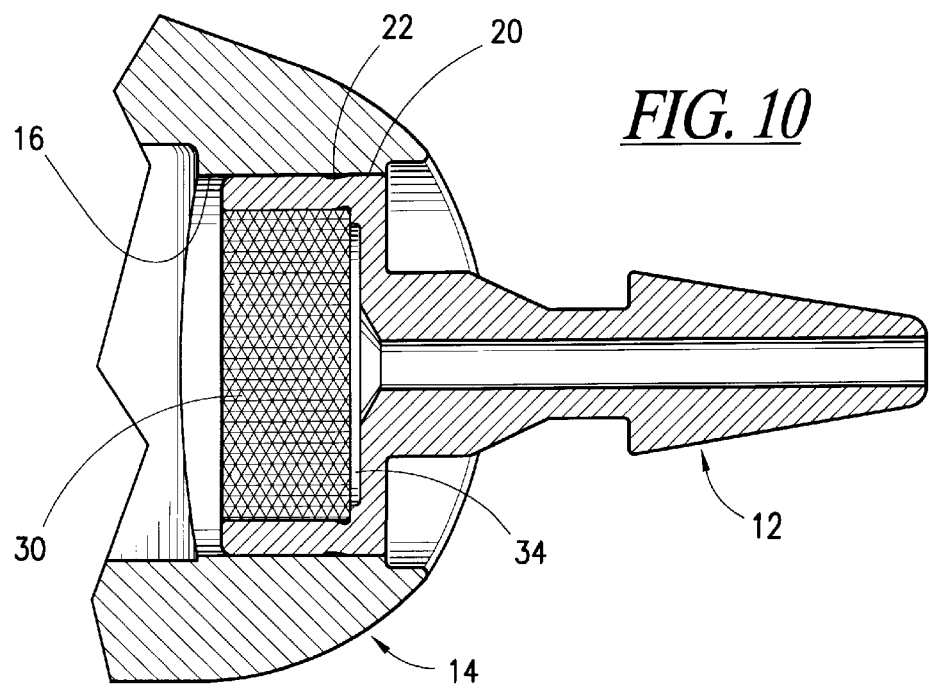
FIG. 10 is a cross-sectional, enlarged view of the housing and connector assembled with filter.

As shown in FIGS. 9 and 10, the connector flange 18 collapses radially when press fit into the housing connector aperture 16 minor diameter (0.156 inch.) The connector major diameter, 0.158 inch, is 0.042 inch wide and is limited to a portion of the collapsible flange 18 that interfaces with the housing aperture 16 minor diameter. The major diameter is located a distance (0.011 inch) from the non-collapsible zone 20. The flange is relieved (0.155 inch diameter) in the non-collapsible zone 20 of the flange and in the transition zone 22 (0.011 inch) between the non-collapsible 20 and collapsible zones 24 of the flange.

The connector flange 18 has an outside radius 26 (0.005 inch) and the housing minor diameter has an inside radius 28

(0.003 inch), both corresponding to the initial engagement of the housing connector interface.

The void 32 in the connector 12 created by the collapsible flange 18 should be filled to diminish residual injection port volume. This may be accomplished with a filter element 30 or a light weight annular plug.

If the void 32 is filled with a filter element 30, either the connector filter chamber or the filter should include a standoff or recess so that fluid can exhaust from a majority portion of the filter's end surface. We show a connector recess 34 in FIG. 10.

A filter 30 is installed in the connector filter chamber 32, inside the collapsible connector flange. The filter 30 may be a sintered material such as metal, plastic, ceramic or other biomaterial. In the preferred embodiment with a titanium housing 14 and connector 12, the filter 30 would be sintered titanium to maintain the same nobility as the housing and connector, or other sintered plastic or ceramic material.

Figure 4:
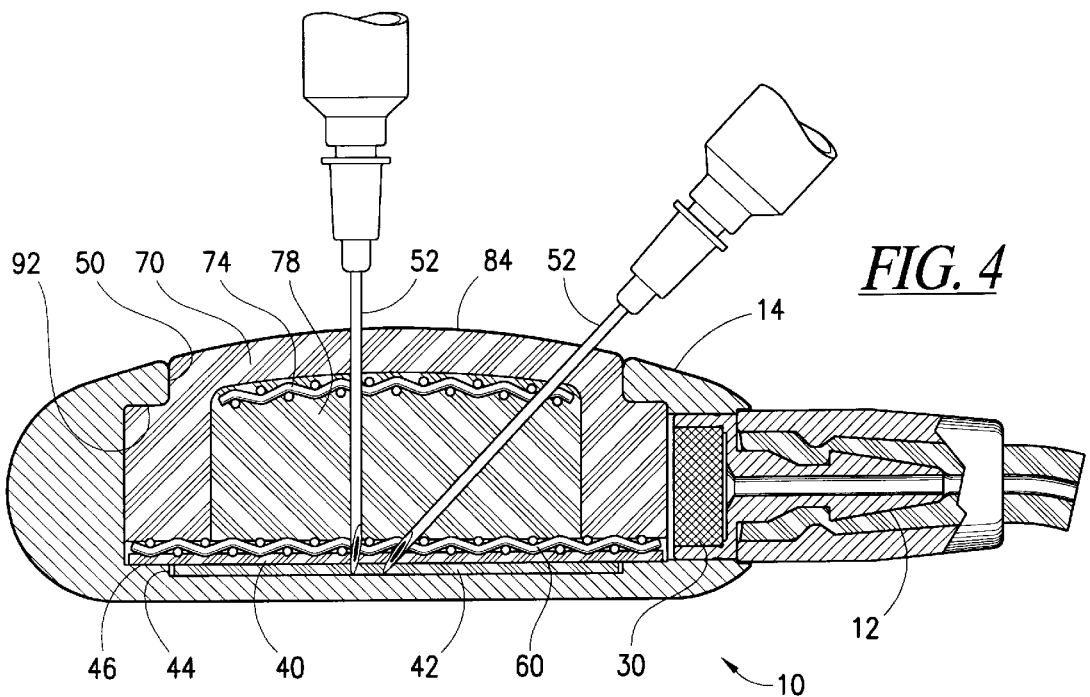
FIG. 4 is a cross-sectional view of the injection port.
Figure 8:
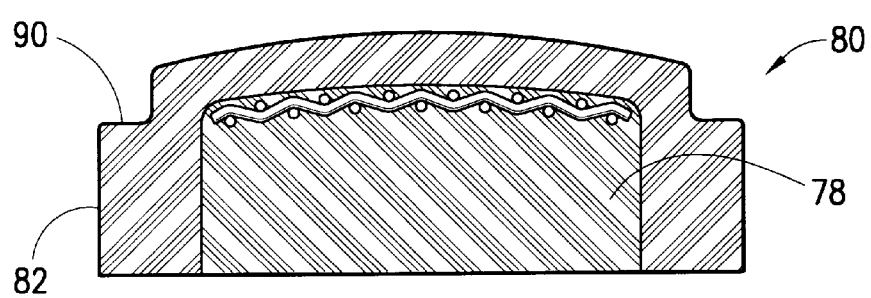
FIG. 8 is an exploded edge view of the disks.
Figure 8:
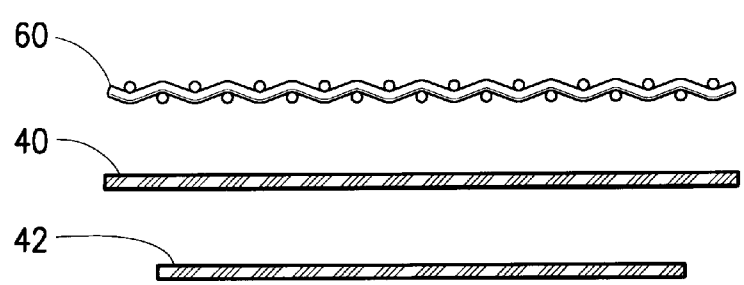

The solid discs 40, 42 shown in FIGS. 4 and 8 that are needle penetrable are die cut from vulcanized sheets of polyester reinforced silicone elastomer. Reinforced silicone discs are used to diminish the potential for fragmentation of the disc as a result of needle damage. The lower disc 42 is bonded to a recess 44 in the base of the housing 14 to assure it remains correctly positioned during subsequent assembly operations. The adjacent disc 40 may also be bonded to the lower disc 40. These needle penetrable silicone discs 40, 42 are randomly deformed to install them through the opening 50 in the housing 14. In the preferred embodiment both discs 40, 42 are 0.020 inch (0.5 mm.) thick for use with a 20–25 gauge infusion needle 52.

The reason for the reduced diameter of the lower solid disc 42 is to provide less resiliency of the stacked components immediately between the housing floor 46 and the horizontal surface 92 of the chamber adjacent the housing entry.

The reason that the second solid disc 40 is the same diameter as the cylindrical portion 86 of the chamber cavity 54, is to provide a resilient material that can partially fill the voids in the non-solid disc 60 to further reduce residual volume.

Figure 4A:
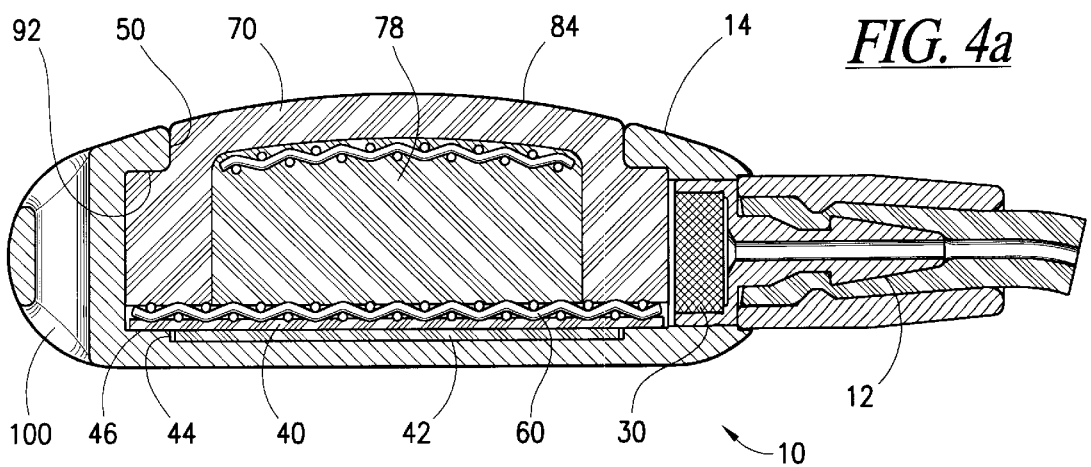
FIG. 4a is a cross-sectional view similar to FIG. 4, without the needles and showing a decrease in residual volume via the solid disks.
Figure 6:
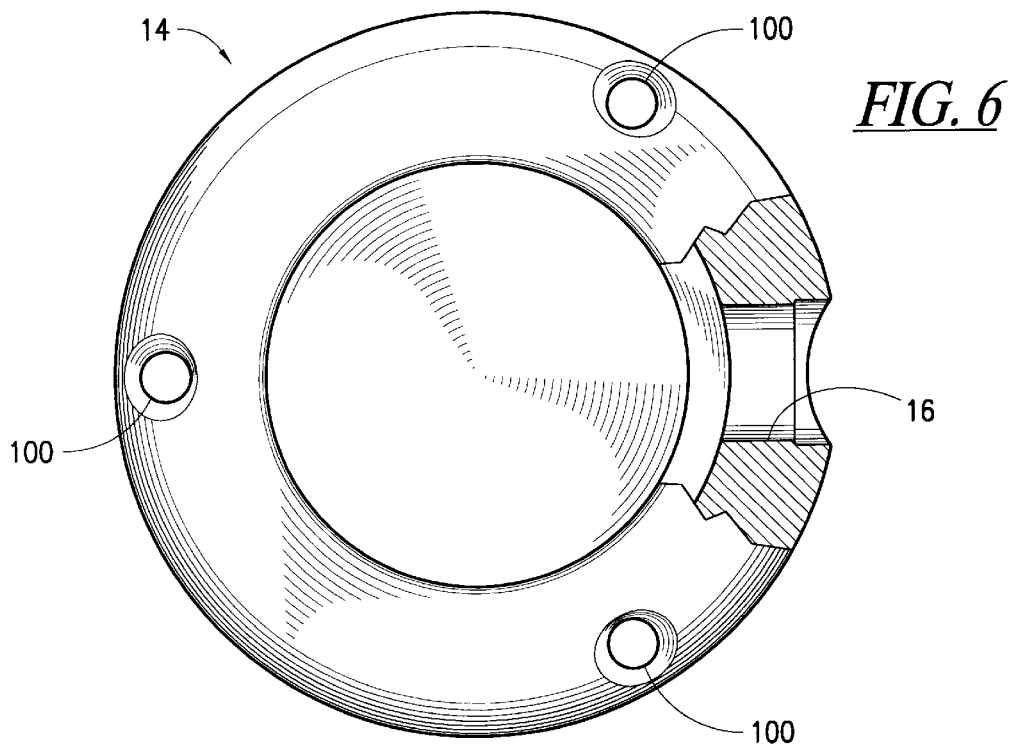
FIG. 6 is a top view of the housing partially broken away.
Figure 5:
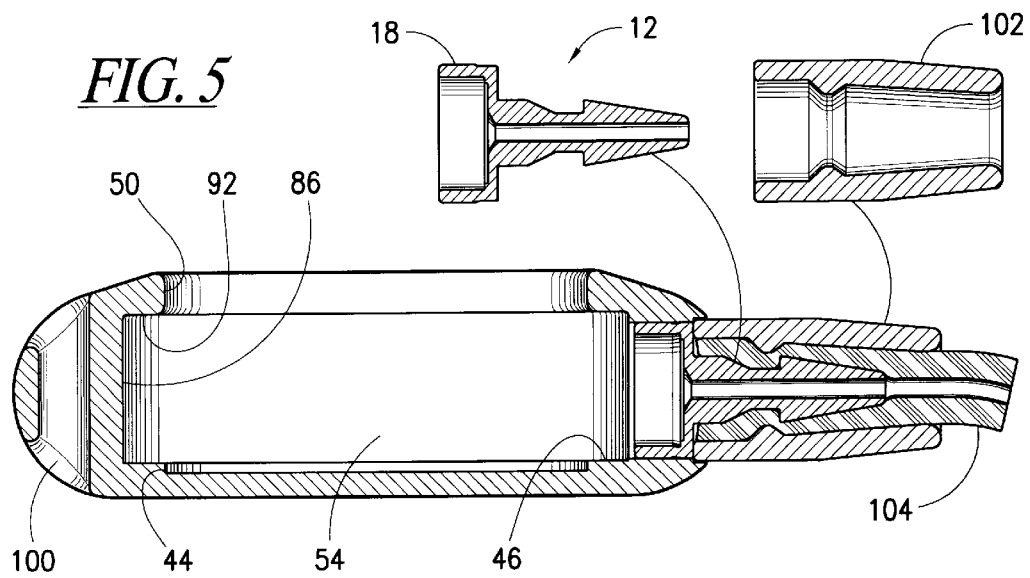
FIG. 5 is a cross-sectional view of the injection port without the septum.
Figure 7:
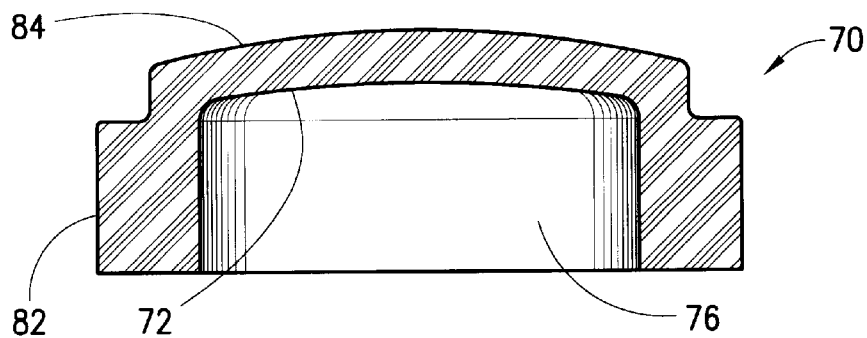
FIG. 7 is an exploded view of the septum assembly.

The non-solid disc 60 is preferably a 0.010 inch diameter wire cloth with a 24×24 mesh plain square weave, that will resist fragmentation from a sharp needle. If the housing 14 and connector 12 are metal, then the wire cloth should be the same material having the same nobility. In the preferred embodiment with a titanium housing 14 the wire cloth is titanium, with a plastic housing it is 316 or 316L stainless steel which is less costly. The disc 60 defines an open mesh channel of very low residual volume. The presence of the lower disk 40 and upper septum against the wire mesh helps to fill in the space defined by the disc 60, thereby decreasing the residual volume even further. This is shown in FIG. 4a. Larger needles and larger drug dosages may require a larger channel. In such cases, the disc 60 may be woven from a thicker wire or two disks 60 may be stacked together.

The wire cloth disc 60 is installed by deforming it in the shape of a spherical radius as it is forced through the opening 50 in the housing 14. The disc 60 can be substantially flattened following installation by grasping the apex of the spherical radius with a small tool or hook and drawing it back toward the housing opening 50.

The septum 70 is compression molded from a platinum cured 80 Shore A Durometer silicone elastomer. A reinforcement disc 74 is formed to the curvature of the inside spherical radius 72 of the molded septum 70. The reinforcement disc 74 is die cut from a 316 stainless steel 0.010 inch Diameter wire cloth with a 24×24 mesh plain square weave. The septum cavity 76 is partially filled with a 20–30 Shore A Durometer RTV silicone adhesive 78. The formed wire cloth 74 is then slowly pushed through the RTV silicone 78 so that air entrapment is minimized or avoided, until the disc 74 is seated against the inside spherical radius 72 of the septum 70. Ideally, the disc 74 is sized so that the die cut wires will engage the interior cylindrical wall of the septum 70 to maintain it's installed position. The remainder of the septum cavity 76 is then filled with RTV silicone adhesive 78. The housing assembly is then floated in a container of water so that the adhesive can self level. The moisture from the water hastens the room temperature vulcanization. Alternately, the assembly can be placed in a fixture which is accurately leveled. The 24×24 mesh and 0.010 inch diameter wire were sized to accept 20–30 gauge needles, larger needles may require different size wire cloth.

A Method of Manufacturing an Implantable Injector Port with Connector

The sub-assembly housing 14 and connector 12 is assembled using an interference fit to collapse the connector flange 18. The major diameter of the connector 12 is press fit into the minor diameter of the housing connector opening 16, to achieve a structural attachment and hermetic seal. The housing 14 is fixtured, with an anvil supporting the internal cylindrical surface of the housing 14. The connector aperture in the housing is placed over a locating bushing in the anvil. The connector is press fit into the housing by applying force to a connector surface that is perpendicular to the direction of the force. As shown in FIG. 10, non-collapsible zone 20 will make light contact, if at all, with housing aperture 16, while the collapsible zone 24 deforms inwardly forming an extremely tight connection to the housing aperture 16. Note that transition zone 22 will still be visible as a gap between the housing aperture 16 and the connector flange 18 after press fitting.

After the connector 12 is installed in the housing 14, the optional filter 30 is inserted into the optional connector filter chamber using a small tool such as a tweezers. The filter 30 may be retained by a close fit with the connector chamber 32 or by the septum sub-assembly 80. Alternately, it could be bonded in the connector filter chamber.

The solid 40, 42 and non-solid discs 60 are installed by deforming them to fit through the housing entry 50. When the disc is not pliable, as is the case with a wire screen 60, it is best deformed into a shape with a spherical radius to reduce the disc diameter as it traverses the housing entry 50. A tool having a spherical radius on the end may be used to drive the disc 60 through the housing entry 50.

The septum assembly 80 is installed by deforming the rim 82 and forcing it into the housing 14. Use of a lubricant such as isopropyl alcohol, for a silicone septum, eases the assembly process. Choice of a lubricant such as isopropyl alcohol diminishes the opportunity for pyrogens in the assembly. The injection port assembly 10 is alternately pressurized and depressurized several times, through the connector 12, to cause the septum dome 84 to expand outwardly through the housing entry 50 and reduce the diameter of the rim 82. This allows the rim 82 of the septum assembly 80 to return to it's normal shape, removes any folds in the septum rim or deformation that may occur during installation, so the septum sub-assembly 80 seats against the housing 14.

The septum rim 82 is sized slightly larger (0.010–0.020 inch) than the diameter of the cylindrical portion of the housing chamber 14, to cause a seal between the cylindrical wall 86 of the housing 14 and the major diameter of the septum sub-assembly 80. Greater compression of the septum sub-assembly 80 was found to be unnecessary. The housing cavity 54 is sized to accommodate the stacked height of the discs 40, 42, 60 and septum sub-assembly 80 with virtually no compression. When the septum sub-assembly 80 is exposed to internal hydraulic pressure, the septum dome 84 is distorted outwardly, the rim 82 diameter is reduced and the seal between the rim 82 and the cylindrical surface 86 of the housing cavity 54 may be interrupted. However, the same internal hydraulic pressure causes the flat portion 90 of the rim 82 to seal against the mating surface 92 of the housing 14. This flat surface 90 may actually shift laterally on the mating housing surface 92 as the septum dome 84 is distorted outwardly, but the fluid seal is maintained.

The septum assembly 80 is fabricated by molding a septum shell, installing a reinforcement 74 on the interior of the septum 70 that is exposed to needle penetration and filling the septum cavity 76 with a low Durometer (hardness) elastomer 78 that will prevent fluid leakage through needle puncture wounds.

The septum shell 70 is molded from a high Durometer elastomer so that the septum rim 82 is stiff enough to resist the hydraulic pressures within the injection port 10 and retain the septum assembly 80 within the housing 14. A reinforcement disc 74 may be cut from a material such as fabric, plastic or metal mesh or cloth, embedded in an elastomeric matrix, and installed in the septum cavity 76 in a secondary molding operation. The cavity 76 is then filled with a low Durometer elastomer 78. Alternately, a reinforcement disc 74 may be placed inside the septum cavity 76, which is then filled with an elastomer 78 that penetrates the reinforcement 74 and affixes it within the septum cavity 76. The low Durometer elastomer 78 may be a platinum or peroxide cured silicone elastomer that is thermally cured. Alternately, an acetoxy cured room temperature vulcanization (RTV) elastomeric adhesive may be used to fill the septum cavity 76.

The injection port 10 may include a plurality of suture holes 100 through the housing 14 which allows the injection port to be sutured to tissue of the body.

The injection port 10 of the invention provides a low profile, large needle target that has very low residual volume due to its unique open mesh channel that is squeezed between a lower disk and upper septum. The spaces between the open mesh are partially filled by the lower disk and upper septum. This low residual volume is very desirable as it means that the drug injected goes to the patient rather than merely filling a large chamber. The channel caused by the disk 60 communicates through to the housing aperture, which itself is of diminished volume due to the presence of a filter, and then out the unique connector 12 to a conventional catheter.

The connector 12 is shown with a particular arrangement of barbs that mate with a corresponding clamp 102 that serve to secure the catheter conduit 104 to the injection port 10. Other connector designs and clamping arrangements may be used although the connector as shown has a very low residual volume to maintain the goal of low residual volume in the system.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A low profile implantable injection port for subcutaneous implantation into the body of a patient, comprising:
    a generally cup-shaped housing having an open end;
    a self-sealing septum mounted to said housing in the open end;
    a low aspect ratio fluid channel within the housing below the septum;
    a needle-penetrable, non-solid component in the fluid channel to form a low residual fluid-retaining volume within the fluid channel, the component having interconnected pathways for allowing fluid to move through the channel; and
    a conduit connector connected to said housing and in fluid communication with said fluid channel for delivering medication from said channel to a patient when attached to a catheter.

2. The injection port of claim 1 wherein the needle-penetrable, non-solid layer includes an open mesh layer of material.

3. The injection port of claim 1 wherein:
    the fluid channel is defined by first and second major fluid-impervious surfaces; and
    the needle-penetrable, non-solid layer of material has first and second surfaces in engagement with the first and second surfaces, respectively, of the fluid channel.

4. The injection port of claim 3 wherein the needle-penetrable, non-solid layer includes an open mesh layer of material.

5. The injection port of claim 4 wherein the septum has a diameter up to about 2 cm and the open mesh layer of material causes the fluid channel to have a residual volume less than about 0.3 ml.

6. The injection port of claim 1 wherein septum has a diameter up to about 2 cm and the non-solid layer of material causes the fluid channel to have a residual volume less than about 0.2 ml.

7. An implantable injection port for subcutaneous implantation into the body of a patient, comprising:
    a housing defining a chamber;
    a self-sealing septum mounted to said housing and closing said chamber;
    an aperture in said housing providing fluid communication between said chamber and the exterior of said housing; and
    a conduit connector connected to said housing and in fluid communication with said chamber for delivering medication from said channel to a patient when attached to a catheter, said conduit connector being press fit into an aperture in said housing, said conduit connector including a collapsible tube which is compressed into said housing aperture.

8. An implantable injection port for subcutaneous implantation into the body of a patient, comprising:
    a generally cup-shaped housing having an open end;
    a self-sealing septum mounted to said housing in the open end;
    a low residual volume channel within said housing below said septum; and
    a conduit connector connected to said housing and in fluid communication with said channel for delivering medication from said channel to a patient when attached to a catheter, said housing having a height less than about ⅓ the diameter of said housing, said septum having a diameter at least ⅔ the housing diameter.

9. The injection port of claim 8 wherein the channel includes a needle-penetrable, non-solid layer of material having top and bottom surfaces, the top and bottom surfaces being in contact with solid needle penetrable disk elements to reduce the void volume of said open mesh disk by encroaching into the mesh.

10. The injection port of claim 9 wherein said non-solid layer of material is positioned above a floor of said housing by said solid needle penetrable disk to correspond to the elevation of a needle cannula when a needle entry into the port is from 0 to about 60 degrees from perpendicular to the port.

11. The injection port of claim 9 wherein the septum has a diameter up to about 2 cm and the non-solid layer of material causes the channel to have a residual volume less than about 0.3 ml.

12. An implantable injection port for subcutaneous implantation into the body of a patient, comprising:

a housing defining a chamber;

a self-sealing septum mounted to said housing and closing said chamber;

an aperture in said housing providing fluid communication between said chamber and the exterior of said housing; and a conduit connector connected to said housing and in fluid communication with said chamber for delivering medication from said channel to a patient when attached to a catheter, said conduit connector having a collapsible flange that is fit into said housing aperture by an interference fit.

13. The injection port of claim 12 wherein said housing aperture is between about 0.0015 to about 0.0030 inches smaller in diameter than the diameter of said connector collapsible flange.

14. The injection port of claim 12 wherein said collapsible flange defines an internal space.

15. The injection port of claim 14 wherein said collapsible flange internal space is substantially filled by an annular plug that reduces the residual volume of said space.

16. The injection part of claim 12 wherein said collapsible flange has an open distal end and a proximal end attached to the main body of said connector, said collapsible flange open distal end having a greater diameter than the diameter of said flange adjacent its proximal end.

17. The injection port of claim 16 wherein said collapsible flange distal end and housing aperture are radiused to initiate collapsing of said collapsible flange during assembly.

18. The injection port of claim 12 wherein said collapsible flange is predisposed to radial deformation and said housing aperture is substantially resistant to radial deformation.

* * * * *

UNITED STATES PATENT AND TRADEMARK OFFICE
CERTIFICATE OF CORRECTION

PATENT NO : 6,039,712
DATED : March 21, 2000
INVENTOR(S) : Terence M. Fogarty

It is certified that error appears in the above-identified patent and that said Letters Patent are hereby corrected as shown below:

Column 6, line 53, delete "channel" and insert therefor --chamber--

Column 8, line 15, delete "part" and insert therefore --port--

Signed and Sealed this

Tenth Day of April, 2001

*Attest:*

NICHOLAS P. GODICI

*Attesting Officer*     *Acting Director of the United States Patent and Trademark Office*